US008625650B2

(12) United States Patent
Lewandowski et al.

(10) Patent No.: US 8,625,650 B2
(45) Date of Patent: Jan. 7, 2014

(54) LIGHT SOURCE, AND OPTICAL COHERENCE TOMOGRAPHY MODULE

(75) Inventors: Jan Lewandowski, Richterswil (CH); Marcus Duelk, Richterswil (CH); Christian Velez, Richterswil (CH)

(73) Assignee: Exalos AG, Schilieren (CH)

( * ) Notice: Subject to any disclaimer, the term of this patent is extended or adjusted under 35 U.S.C. 154(b) by 0 days.

(21) Appl. No.: 13/260,995

(22) PCT Filed: Jan. 22, 2010

(86) PCT No.: PCT/CH2010/000015
§ 371 (c)(1),
(2), (4) Date: Oct. 6, 2011

(87) PCT Pub. No.: WO2010/111795
PCT Pub. Date: Oct. 7, 2010

(65) Prior Publication Data
US 2012/0026503 A1    Feb. 2, 2012

Related U.S. Application Data

(60) Provisional application No. 61/166,470, filed on Apr. 3, 2009.

(51) Int. Cl.
*H01S 3/08* (2006.01)
(52) U.S. Cl.
USPC ............. 372/102; 372/99; 372/98; 372/92
(58) Field of Classification Search
USPC ............. 372/69, 75, 92, 98, 99, 102, 108; 250/363.04; 378/4, 21
See application file for complete search history.

(56) References Cited

U.S. PATENT DOCUMENTS

| 6,608,847 | B2* | 8/2003 | Zhang et al. ............ 372/20 |
| 7,099,358 | B1 | 8/2006 | Chong |
| 7,292,515 | B2* | 11/2007 | Holtslag et al. ........... 369/94 |
| 2003/0223471 | A1* | 12/2003 | Baney ................. 372/92 |
| 2004/0101016 | A1 | 5/2004 | McDonald et al. |
| 2006/0039424 | A1* | 2/2006 | Thoma et al. ........... 372/29.02 |
| 2006/0056464 | A1 | 3/2006 | Chong |
| 2008/0298402 | A1* | 12/2008 | Rossi et al. ............ 372/20 |
| 2009/0027689 | A1* | 1/2009 | Yun et al. ............. 356/511 |
| 2010/0091804 | A1* | 4/2010 | Musio et al. ............ 372/20 |

FOREIGN PATENT DOCUMENTS

| EP | 0347213 | | 12/1989 |
| EP | 0550929 | | 7/1993 |
| EP | 2004007102 | * | 2/2006 |
| EP | 2042086 | | 4/2009 |

(Continued)

*Primary Examiner* — Kinam Park
(74) *Attorney, Agent, or Firm* — Rankin, Hill & Clark LLP

(57) ABSTRACT

A swept wavelength light source is provided, the light source includes a semiconductor gain device operable to provide amplification, an optical retarding device, the retarding device having a block of material, a beam path with a well-defined beam path length being defined for light within the block of material produced by the gain device, a wavelength selector, and the gain device, the retarding device and wavelength selector being mutually arranged on the base so that a resonator is established for light portions emitted by the gain device and selected by wavelength selector; this does not exclude the presence of further elements contributing to the resonator, such as additional mirrors (including resonator end mirrors), lenses, polarization selective elements, other passive optical components, etc.; wherein the beam path in the retarding device is a part of a beam path of the resonator.

75 Claims, 8 Drawing Sheets

(56) References Cited

FOREIGN PATENT DOCUMENTS

| | | |
|---|---|---|
| JP | 3-148890 | 6/1991 |
| JP | 2003-021576 | 1/2003 |
| JP | 2005-17410 | 1/2005 |
| JP | 2005-202039 | 7/2005 |
| JP | 2007-273834 | 10/2007 |
| JP | 2009-31238 | 2/2009 |
| WO | 00/24095 | 4/2000 |
| WO | 02/09244 | 1/2002 |
| WO | 2005/001401 | 1/2005 |
| WO | WO 2006002663 A1 * | 1/2006 |
| WO | 2009/097740 | 8/2009 |

* cited by examiner

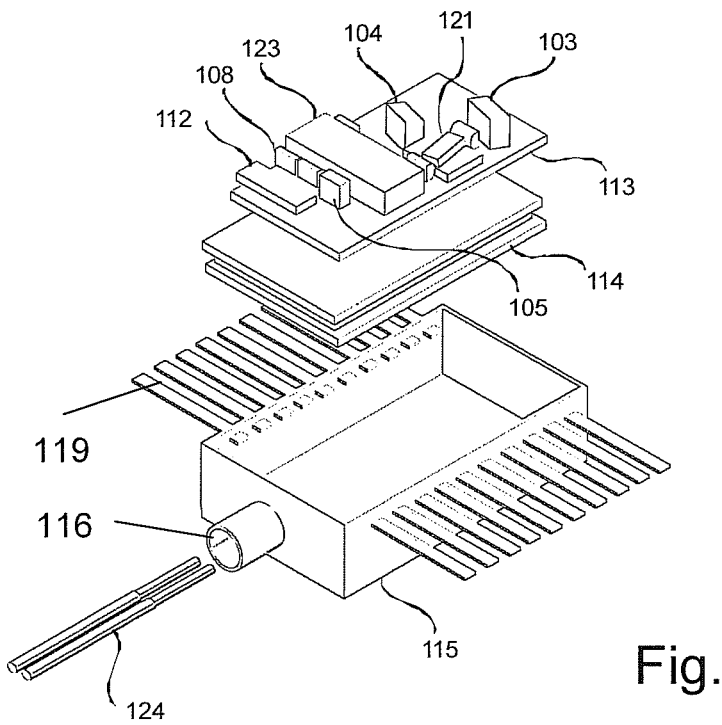
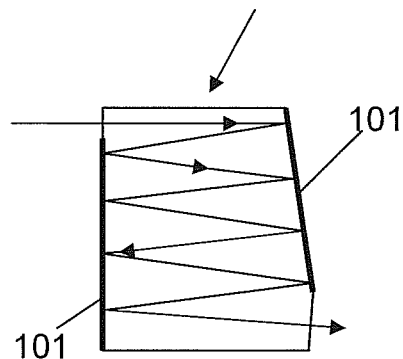
Fig. 8
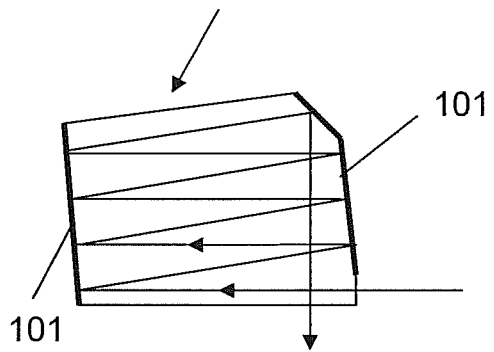
Fig. 9a

LIGHT SOURCE, AND OPTICAL COHERENCE TOMOGRAPHY MODULE

FIELD OF THE INVENTION

The invention is in the field of light sources, i.e. of sources of electromagnetic radiation in the infrared, visible, and ultraviolet part of the electromagnetic radiation spectrum. More concretely, the invention concerns a light source, an optical coherence tomography apparatus, and an optical coherence tomography module.

BACKGROUND OF THE INVENTION

Optical Coherence Tomography (OCT) is an emerging technique for sub-surface imaging with medical, biological and other applications. OCT is the optical analog of ultrasound but takes advantage of the shorter wavelengths of light to achieve higher resolution images. Potentially the wavelength ranges of interest lie within the visible to near infrared regions of the spectrum from 400-2000 nm. Currently, there are four wavelength ranges of interest in OCT centered around 850 nm, 1050 nm, 1300 nm and 1550 nm. OCT systems comprise (1) a broadband light source, (2) an arrangement of optical components for directing the emitted radiation to a sample and to a reference mirror and (3) an optical arrangement for measurement of interference of light reflected from the sample and light reflected from the reference mirror. For state-of-the-art Time Domain OCT (TD-OCT) systems, the broadband source is a superluminescent light emitting diode (SLED) which emits light in a broad spectrum of wavelengths (40-200 nm bandwidth), and the sub-surface imaging depth is controlled by scanning the position of the reference mirror. Constructive interference only occurs when the path-lengths between the reference mirror and sample reflectors are equal within the coherence length of the light source. Fourier or Frequency domain OCT (FD-OCT) makes use of spectral frequency information, for example by decoding the interference using a dispersive element and a CCD detector array or Spectrometer (Spectral Domain OCT or SD-OCT). Another FD-OCT technique, requiring a simpler detection system, uses spectral encoding in time by spectrally scanning a narrow bandwidth light source (Swept Source OCT or SS-OCT).

According to the state of the art, in SS-OCT, a tunable laser is used as the light source. SS-OCT has been demonstrated to have major signal to noise advantages over TD-OCT (see Choma et al, Optics Express, vol. 11, 2003 pp. 2183-2189). To realize its advantages over TD-OCT, swept source OCT systems require tunable light sources that can be swept across a wavelength range at high frequencies of 20-400 kHz. Since the imaging depth required for the interferometers of these systems is related to the coherence length of the light source, this also sets the requirements for the linewidth and line spacing of the light source.

Various methods have been employed to achieve swept sources for SS-OCT. Among these are cascaded Distributed Feedback (DFB) lasers (US 2008/0037608), multi-wavelength lasers (US 2007/0002327), diffraction gratings and grating pairs (US 2008/0002209, U.S. Pat. No. 7,006,231), fiber laser ring cavities (US 2006/0193352) external cavity lasers employing Fabry-Perot filter tuning elements in both ring and linear configurations (U.S. Pat. No. 7,242,509, US 2006/0215713). Of these methods, the latter MEMS Fabry-Perot filter approaches are most applicable to integration within compact optical modules. In this case, the MEMS device performs both wavelength selection and wavelength sweep functions and needs to be manufactured to tight mechanical tolerances. The Fabry-Perot MEMS device is essentially a linear transducer that has speed limitations and is susceptible to variations in reflectivity, parallelism, flatness and filter cavity thickness over the tuning bandwidth. Variation in the latter parameter results in variation in bandwidth, coherence and imaging depth during a wavelength sweep of an SS-OCT system.

Another method (US 2007/0183643) employs a MEMS tunable mirror integrated with a Vertical Cavity Surface Emitting Laser (VCSEL). Integration of these elements, however, is difficult to manufacture and has yet to be realized.

Simpler and more versatile designs are based on external cavity lasers where the filtering and wavelength sweep functions are performed by a grating and a rotating or scanning mirror (U.S. Pat. No. 6,111,645, U.S. Pat. No. 5,907,423, US 2007/0276269, US 2007/0239035, US 2007/0064239, US 2008/0043244, US 2004/0213306). These designs are versatile, since they can relatively easily be adapted for other wavelength ranges. Swept-source OCT applications require the swept source to have a coherence length that is above a certain minimum value and below a certain maximum value. The minimum value is related to the minimum imaging range of the application (imaging range is half the coherence length), for example 6 mm for retina imaging or up to 25 mm for imaging of the whole eye from the retina to the cornea. However, it would not be good to take a swept source that has a too long coherence length because then any kind of reflective object within the imaging range will cause unwanted interference signals. Therefore, multimode laser operation is required in order for the spectral bandwidth of the external cavity laser to have a certain minimum value. Single mode operation would not guarantee that the coherence length does not exceed a certain maximum acceptable value. A consequence of this minimum spectral bandwidth is a relatively long cavity length. In general, this lies in a range 3-30 cm, depending upon the wavelength range and the number of modes in the cavity. This cavity length requirement restricts the miniaturization of the swept source. Ideally, the swept source should easily be qualified and integrated into compact SS-OCT systems. Also, a too long cavity length makes the wavelength tuning slow, limiting the sweep rate.

BRIEF SUMMARY OF THE INVENTION

It is an object of the invention to provide a 'swept-source' light source for OCT or other applications of swept sources, that overcomes drawbacks of prior art light sources. It is a further object to provide an optical coherence tomography apparatus, an optical coherence tomography module.

In accordance with a first aspect of the invention, a swept light source is provided, the light source comprising:
  an optical module casing with at least one optical feedthrough and a plurality of electrical feedthroughs,
  a semiconductor gain device operable to provide light amplification;
  a wavelength selector; and
  light re-directors;
  the gain device, the light re-directors and the wavelength selector being mutually arranged in the optical module casing so that a multimode resonator is established for light portions emitted by the gain device and selected by wavelength selector;
  wherein the resonator is an external cavity laser resonator and for example comprises light path portions in free space;

and wherein one end reflector of the resonator is partially transmitting and wherein light transmitted through this one end reflector is at least partially directed to exit through the optical feedthrough.

In preferred embodiments, the swept light source according to the first aspect of the invention comprises the features of a swept light source of a second aspect of the invention and comprises an optical retarding device as described hereinafter. In other embodiments that may be advantageous, too, the swept light source according to the first aspect of the invention comprises a folded cavity in which the light is directed back and forth on different path portions within the module casing a plurality of times.

The optical feedthrough may comprise a fiber or a plurality of fibers, or it may comprise a window through which radiation is directed.

An advantage of the approach according to the first aspect of the invention is that the light source components—and possibly elements of further devices such as intensity detector(s), beam splitter/combiner, a wavemeter and/or even a reference arm of an OCT set-up—are integrated in a common package. The devices integrated in the package preferably include the moving parts such as a MEMS grating or an MEMS mirror.

The approach brings about advantages in terms of compactness, handling, manufacturing cost and calibration effort by the user. In accordance with preferred embodiments, the devices of the package have a common thermoelectric cooler that is in contact with a mount on which a plurality of the components within the module casing are arranged. This brings about further advantages in terms of stability and reproducibility as well as being advantageous in terms of manufacturing complexity.

In contrast to optical packages as light sources of the prior art, the first aspect of the invention proposes to provide a swept light source with a wavelength selector (that may comprise a movable MEMS mirror and a grating or a Fabry-Perot filter tuning element (for example a Fabry-Perot MEMS device), or a rotating scanning mirror and a grating, etc.) and proposes multimode operation. Multimode operation makes possible that the coherence length can be controlled not to exceed a certain maximum acceptable value. In addition, single mode operation—unless the cavity length is adjusted during tuning, which would require complicated set-up, mode hopping occurs: Mode-hopping means that the laser will turn off lasing operation for a short period of time and then turn on lasing operation again once the tunable filter coincides with the next lasing mode. The turn-on process of a laser, however, can be a relatively slow process (relative to the fast sweep rates that are required for SS-OCT applications) because stimulated laser emission has to build up from spontaneous emission and amplified spontaneous emission and therefore stable laser operation with low noise and good signal-to-noise ratio will require several round-trips in the laser cavity. Therefore, again, a multi-mode laser cavity is advantageous for fast wavelength tuning because the laser cavity can be kept lasing during the wavelength sweep. However, the laser cavity should not be too long (unless special techniques like Fourier-domain mode-locking (FDML) are used) because the associated long round-trip times would prohibit fast wavelength tuning again.

According to a second aspect of the invention, a swept wavelength light source is provided, the light source comprising:

a semiconductor gain device operable to provide light amplification, an optical retarding device, the retarding device comprising a block of material, a beam path with a well-defined beam path length within the block of material being defined for light produced by the gain device, a wavelength selector, and a base, the gain device, the retarding device and wavelength selector being mutually arranged on the base so that a resonator is established for light portions emitted by the gain device and selected by the wavelength selector; this does not exclude the presence of further elements contributing to the resonator, such as additional mirrors (including resonator end mirrors), lenses, polarization selective elements, other passive optical components, etc.;

wherein the beam path in the retarding device is a part of a beam path of the resonator.

Throughout this text, the term "light" is used to refer to electromagnetic radiation in the infrared, visible and ultraviolet part of the spectrum. The light source according to the invention is especially suited for producing light in the near infrared or visible part of the spectrum.

The retarding device in embodiments of the second aspect of the invention thus is a part of an optical external cavity laser resonator. The optical path in the retarding device preferably constitutes a significant, substantial part of the optical resonator length. The path length in the retarding device (thus also the number of reflections) is well-defined by the arrangement. For example, the optical path length in the retarding device is at least 30%, at least 40% or at least 50% or 60% of the optical resonator length (the optical lengths being defined as the physical path lengths multiplied by the local index of refraction). The number of passes within the retarding device is for example at least 4, preferably at least 6 or even 8 or more. In many embodiments, the fraction of the path length taken up in the retarding device is to be just high enough to enable the integration of an optical cavity within an optical package. There are embodiments of the optical retarding device in which the light traces within the device are not necessarily parallel. In general, a "pass" is a path portion inside the retarding device in between two subsequent reflections.

The optical resonator length is often between 1 cm and 1 m, in many cases between 3 cm and 30 cm.

In embodiments of the first and/or of the second aspect, the gain device, the retarding device and the wavelength selector are arranged on the common base, and in many embodiments they are packaged, in an optical module package, to constitute an optical module. The optical module package forms a package housing with at least one optical feedthrough and with a plurality of electrical feedthroughs for feeding and controlling the components within the package and, if necessary, for reading out signals from within the package. The optical package, for example, comprises a common thermoelectric cooler, and the optical devices of the packaged are all in direct thermal contact with the thermoelectric cooler, i.e. are for example on a common heat conducting carrier plate that is in direct physical contact with the thermoelectric cooler. The optical package is for example closed—and possibly sealed—against the outside so that the components on the base are at most accessible by the electrical feedthroughs and/or the optical feedthroughs. The retarding device enables miniaturisation of the tunable external cavity arrangement so that it can be assembled into standard optical modules such as, for example, those known in the art as butterfly packages. The relatively simple optical arrangement is easily adaptable to operate at all the wavelength ranges of interest for SS-OCT by employing suitable gain blocks (or, as the case may be, resonator geometries of a free-space resonator) and optical coatings on components.

Despite achieving multimode operation and according cavity dimension requirements, the dimensions of the overall package are compact, with a two-dimensionsal extension (in the plane of the mount) of preferably not greater than 22 mm*60 mm, in a preferred embodiment not greater than 13 mm×30 mm. For example, an overall extension is not greater than 22 mm*60 mm*20 mm, preferably not greater than 20 mm*40 mm*20 mm, especially not greater than 15 mm*35 mm*10 mm or not greater than 13 mm*30 mm*10 mm.

In many embodiments of the second aspect, the retarding device comprises a plurality of reflective surfaces for reflecting back and forth light portions propagating in the block of material. The retarding device may be a block of material, for example of Silica or $LiNbO_3$ or any other suitable material transparent for the light wavelengths concerned. The block may have two opposing surfaces that may be essentially parallel and that may be at least partially coated to be reflective. Suitable coatings may include metal coatings, dielectric coatings or other reflective layers. The light path within the retarding device may be defined by at least one of:

the angle of incidence and geometrical optics, and a waveguiding structure formed within the block of material.

In a special embodiment, the retarding device may comprise a circulating optical waveguide design.

In another embodiment, the retarding device comprises a body of a material transparent to the light to be used. The body has a plurality of plane facets that include facets that are at an angle different from 90° with respect to each other. At least two of the facets are at least partially reflective for the light in the resonator (by having a reflective coating and/or by the light impinging on an angle shallow enough to exceed the angle of internal reflection) and reflect light impinging on the facet from an inside of the body back into the body. The body is designed and arranged so that the light path in the resonator is perpendicular to the respective end facet at non-reflective entrance and exit end facets (the distinction between the entrance and the exit is somewhat arbitrary: in the resonator the light will enter and exit both, through the entrance and the exit facets) and is non-perpendicular to the facets at least partially provided with a reflective coating.

In preferred embodiments, the retarding device is designed so that at least one, preferably all reflections in the retarding device are caused by the light being incident on the facet at a low angle, for example below 50° or below the maximum angle for total internal reflection. By this measure, insertion losses that, for reflective coatings, are caused by the coatings being non-ideal are avoided. Also in these embodiments, the respective facets may in addition be provided with a highly reflective coating.

The body of transparent material may, for example, be made of glass (a suitable material especially for embodiments where the light for being internally reflected impinges on a low angle), silica, a polymer, a semiconductor compound, etc.

For example, the retarding device body has a generally rhomboid shape with a first facet and a second facet not parallel to the first facet. The retarding device is arranged so that the angle of incidence on the first facet is perpendicular. The light path in the retarding device is defined by geometrical optics. At an exit point of the light path from the retarding device, the second facet or the first facet comprises an angled portion so that when exiting the light path is perpendicular to the surface through which it exits.

In a further embodiment, the retarding device may comprise an optical waveguide design with waveguides defined at different vertical planes to enable longer beam path lengths in the retarding device. Such an optical waveguide design also facilitates coupling to optical components having optical axes at different levels.

The retarding device may include one or more optical directional couplers. Such a directional coupler may be used for splitting the light in the retarding device between a resonator path and a monitoring path, between a sample output and a reference output, and/or also between an input and an imaging output.

The wavelength selector, in embodiments of the first and/or the second aspect, may comprise a scanning Micro-Opto-Electro-Mechanical Systems (MOEMS) mirror (sometimes also termed MEMS mirror) cooperating with a wavelength selective element, such as a grating. The MOEMS mirror and grating component are arranged to provide the tunable feature of the external cavity laser. The grating acts as a filter to select a narrow range of wavelengths for the cavity. The MOEMS mirror is scanned to vary the incident angle of light onto the grating such that the center wavelength of the narrow range of wavelengths can be varied. Alternatively, the grating could be integrated on the surface of the MOEMS scanning device.

MOEMS devices (mirrors or, as an alternative for example also a MOEMS prism could be used) feature the advantage of having dimensions suitable for integration on the common base and in the optoelectronic package, without any negative influence on the overall size.

Also, in some embodiments, the integrated swept wavelength light source also comprises a monitor, such as a monitoring photodiode, also arranged on the common base. The monitor is arranged so that a representative portion of the light circulating in the resonator is coupled out of the resonator and directed onto the monitor. The monitor comprises an electronic monitor output that is contactable by way of an electrical feedthrough from outside of the module so as to provide the possibility of an electronic control of the light source.

In embodiments of the first and/or second aspect of the invention, which embodiments may, depending on the application, be advantageous, the gain device has a reflective end facet that is used as a resonator end mirror. For example, the partially transparent laser outcoupling mirror may be replaced by the (partially) reflective end facet of the gain device. Semiconductor gain devices with a reflective end facet correspond to reflective semiconductor optical amplifiers (R-SOAs). By the simple measure of using an R-SOA as both, gain device and outcoupling mirror, the efficiency of the device may be improved. This is because in a laser resonator, there are coupling losses when the light circulating in the resonator is coupled into the gain device. If, instead of a gain device placed in an interior of the resonator, an R-SOA is used, the light has to be coupled into the gain device only once in every roundtrip in the resonator instead of twice. This may bring about a substantial reduction of the cavity loss and may therefore improve the swept-wavelength light source in power, tuning speed, tuning range, signal-to-noise ratio and/or other optical parameters.

Now focusing on the second aspect of the invention, embodiments of the second aspect may be implemented according to one of the following designs:

In a first arrangement type, the retarding device is positioned between the gain device and the wavelength selector;

In a second arrangement type, the retarding device is positioned to one side of the gain block and the wavelength selector.

In each case, "side" refers to an optical beam path in the resonator.

In the case of the first arrangement type, the gain block used may be a reflective semiconductor optical amplifier (that in itself may be a resonator). Optical radiation propagates along a path which extends from the partially-reflective (for example 3-80%) facet of the R-SOA through the retarding device and is, for example, reflected by the MEMs mirror onto the grating. The optical path length between the R-SOA and the grating defines the length of the resonator (cavity) and the coherence properties of the swept source. The external cavity laser light is coupled to an optical fiber at the partially reflective semiconductor optical amplifier. Alternatively, in the case of the first arrangement, the gain block used may be a (non-reflective—for example<0.5%) semiconductor optical amplifier (SOA), a separate outcoupling mirror being provided. Embodiments with the R-SOA are, however, more compact.

In the case of the second arrangement type, the gain block used may be a semiconductor optical amplifier (SOA). In this case, optical radiation propagates along a path extending from a reflective coating on the retarding device through the SOA and is (for example) also reflected by the MEMS mirror onto the grating. The optical path length between the reflective coating of the retarding device and the grating defines the length of the cavity and the coherence properties of the swept source. The external cavity laser light is coupled to an optical fiber at the retarding device. In alternative embodiments, a separate outcoupling mirror on the other side of the retarding device (compared to the SOA) defines an end of the cavity.

In a special embodiment of the second arrangement, the retarding device provides an additional interferometer with outputs that are coupled to an optical fiber or to a plurality of optical fibers.

In embodiments of the first and/or of the second aspect, the light source may further comprise an electronic controller to regulate and adjust its performance. This may comprise a controlling device, for example including controlling electronic components and/or controlling software and/or firmware running on generic hardware, such as on a PC, a microprocessor, a microcontroller, or an FPGA. The controller is connected or connectable to the components on the base by electrical contact means, such as the electrical feedthroughs.

The invention also concerns an optical coherence tomography apparatus, the apparatus comprising:

a light source according to the first and/or second aspect of the invention;

an interferometer in optical communication with the light source;

an optics unit, the optics unit suitable for focusing a light portion originating from the light source onto a chosen location of a sample, and for performing a scan, in which said location and the sample are moved relative to one another;

the interferometer being operable to combine a portion of light produced by the light source and returned from the sample with a portion of light produced by the light source and returned to the interferometer via a reference path; and a detector unit positioned to receive combined light from the interferometer.

In this, "interferometer" refers to at least the portion of an interferometer that re-combines light coming from two paths. While other, physical definitions demand all elements that constitute the light paths—including the sample from which light portions are emitted back upon illumination, reflecting mirrors, and the detector—to belong to the interferometer, this is not the definition used in this text. In the following, therefore, the interferometer (or interferometer portion) that re-combines light coming from two paths is sometimes also referred to as "portion of an interferometer".

As discussed above, there are embodiments of the light source, where the retarding device includes at least one directional coupler. These include embodiments where the directional coupler or one of the directional couplers comprises four waveguide branches:

A first branch coupled to the resonator;

A second and a third branch coupled to two output fibers, light coming from the first branch being split between the second and third branches; and A fourth branch coupled to a detector (such as a sensitive photodiode), wherein light portions coming from the second and third branches interfere in the directional coupler and some of the interfering light portions are coupled into the fourth branch (others might then be coupled back into the first branch).

If the optical coherence tomography apparatus of the above-defined kind comprises a light source according to such an embodiment, the portion of the interferometer (being formed by the directional coupler) is integrated in the light source, and so is optionally the detector. Then, the optics unit may have to be merely provided with the integrated light source and detector module.

The invention further also refers to an optical coherence tomography module for an optical coherence tomography apparatus, the module comprising:

a light source according to the first and/or second aspect of the invention; and further comprising a sensor arrangement being positioned and equipped for sensing properties of light produced by the light source and/or of performing a measurement of an interferometer signal.

In an embodiment, the module may, in addition to the light source, comprise:

a portion of an interferometer in optical communication with the light source and operable to combine a portion of light produced by the light source and returned from a sample with a portion of light produced by the light source and returned from a reference path; and a detector unit (being the sensor arrangement or belonging to the sensor arrangement) positioned to receive combined light from the interferometer.

In embodiments of the above-discussed kind with integrated interferometer and detector, the module is the integrated light source. In other embodiments, the module may, in addition to the packaged light source, comprise a separate, but potentially fixedly attached interferometer and detector.

The module may further comprise, externally to the module casing, an electronics unit that includes an analyzer and/or evaluator for evaluating data produced by the sensor arrangement.

The light source in accordance with any aspect of the invention may further incorporate measures for ensuring that the sweeping is linear or approximately linear. In a resonator, if the moving part(s) is/are just driven by an electrical signal linear in time, or of a resonant MEMS structure, for example driven by a clock-like signal to oscillate sinusoidally, is used, often a non-linear frequency dependency of the output radiation will result. A linear sweeping over time in the frequency domain (in k-space), however, is advantageous for OCT applications. The measures incorporated may include one or more of the following:

(i) the moving part(s) of the wavelength selector (such as the MEMS mirror(s)) is/are driven with a characteristic ramp pattern in order to provide such linear sweeping in the frequency domain;

(ii) The diffraction grating of the wavelength selector (in embodiments where the wavelength selector comprises a diffraction grating) as a non-constant pitch (grating constant) over the range the light beam is sweeping across. The non-constant pitch—a kind of special "chirp"—is chosen so that a more linear frequency sweep in time is achieved.

(iii) The angle of incidence onto the grating is changed by an optical component between the moving part (the tuning element, e.g. mirror) of the light source and the grating. Such an additional optical component would again change the sweep characteristics over time and make it more linear in the frequency domain.

In accordance with a third aspect of the invention, an optical module is provided, the module comprising:

a swept laser light source, for example in accordance with the first and/or the second aspect of the invention, and a wavemeter, the wavemeter being operable and positioned to issue a measure of the wavelength and/or frequency of light output by the light source, the wavemeter comprising:

a beam tap capable of directing a tapped beam portion of a primary beam generated by the light source on a path separate from the main beam path, a filter device with a wavelength dependent transmission characteristics, the filter device being arranged so that the tapped beam portion impinges on the filter, a first wavemeter detector arranged to detect an intensity of a fraction of the tapped beam portion transmitted through the filter device, and a second wavemeter detector arranged to detect an intensity of a fraction of the tapped beam portion not transmitted through the filter device.

The electronics unit then may be configured to calculate the quantity $(I_T-I_R)/(I_T+I_R)$ from which, given the known or initially measured filter characteristics, the wavelength or a related quantity may be calculated.

The filter device is chosen so that in the light source wavelength range, in which the light source output wavelength sweeps, the filter characteristics has a pronounced wavelength dependence. Preferably, in the light source wavelength range, the filter transmission characteristic is a strictly monotonous function of the wavelength. The difference between the transmission at the lowest wavelength of the wavelength range, and the transmission of the highest wavelength of the wavelength range is then preferably as high as possible. The filter may be a high-pass filter or a low-pass filter. However, a in preferred embodiments, the filter is a bandpass filter, the passband of which is offset relative to the wavelength range, so that the wavelength range is in a sloped portion of the filter transmission characteristics. There are bandpass filters available that have, within the wavelength range being used for example for swept-source OCT, a steep characteristic.

In prior art of SS-OCT systems an optical filter with a periodic transmissive or reflective response in the frequency domain (k-space), for example a Mach-Zehnder interferometer or a Fabry-Perot filter, is used to generate an optical k-clock, that is a signal that exhibits a local maximum or peak each time the swept source has changed the frequency by a fixed amount that is identical to the free-spectral range of such periodic optical filter. This optical k-clock signal is detected by a photodetector and converted into an electrical k-clock signal that is then synchronized with other clock signals of the SS-OCT system responsible, for example, for sampling the received OCT signal from the interferometer.

In contrast to prior art wavemeters, that for example are based on the Michelson or Fizeau interferometer principle, however, the proposed wavemeter according to the third aspect of the invention is simple, robust, has no moving parts, and the output signals are easy to analyze.

Also, the signal from the wavemeter is independent of the optical output power of the swept laser and hence a true measure of the wavelength or frequency.

In contrast to k-clocks of prior art OCT modules, a measure for the absolute value of the wavelength is measured, and not only a relative measure. Further, the measurement of the wavelength values can be done at any time, i.e. with any sampling rate set by a separate clock. Thus, it is possible to use a clock (system clock) that is used for sampling the measurement of the signal, for example the intensity I of an OCT interference signal to be measured, or another clock in time with such a system clock. Synchronization of the device is much easier than in prior art approaches where the signal peeks of the k-clock itself had to serve as synchronizing signal. If the wavemeter is sampled synchronously with the wanted signal, one obtains directly data pairs of (wanted) intensity data and of the wavelength at which the wanted intensity data was generated. In accordance with a preferred embodiment, the electronics unit of the module thus further comprises a clock, the clock being operable to trigger a sampling of the first and second wavemeter detector signals. The clock may further be operable to trigger a sampling of a wanted intensity signal.

It has been known to use wavelength selective filters for stabilizing lasers. Embodiments of the third aspect of the invention, however go in another direction by proposing to use such a filter as a component of a wavemeter that can be sampled synchronously with the signal.

Embodiments of optical modules according to the first, second an/or third aspect of the invention may further optionally comprise one or a combination of the following:

a DC signal offset compensation: Such a DC signal offset compensation may be based on the principle of heterodyne balanced detection. It may eliminate the effect of primary light source intensity variations, that for example may arise periodically with the sweeping frequency (if the produced radiation intensity has some wavelength dependence) or slowly as a reaction to changing parameters such as a temperature change etc. For example, the two outputs of the beam splitter/combiner may be used and directed at two detectors, and the measured intensities at these detectors are subtracted from each other. Since the interference signal occurs 180° degrees out of phase at the two detectors, subtracting the two signals adds the heterodyne interference signal but subtracts excess noise.

A beam splitter/combiner of an OCT device (OCT interferometer) that is used to split a primary beam between a sample arm and a reference arm and to combine light portions coming back from the sample arm and the reference arm and to direct combined, interfering light portions onto a wanted signal intensity detector (which detector is preferably also an element of the optical module). Optionally, the optical module may further comprise the reference arm with light deflecting and/or light guiding means that direct the reference light beam from the beam splitter/combiner on an optical path with a defined optical length back to the beam splitter/combiner. By this, the optical module may become an 'OCT engine', i.e. a device that outputs a sample radiation (of an OCT interferometer sample arm) and comprises the means for bringing to interfere and analyzing the radiation coming back from the sample in the sample arm.

A beam splitter, for example of equal or approximately equal intensity. The module may then further comprise two beam splitters/combiners and twice according detection means (that optionally may include DC offset compensation)

and, optionally, two reference arms, as well as according optical (and electrical) output/inputs. By this, the optical module is suitable for simultaneously carrying out two OCT measurements by means of a single light source.

All of these optional features may be incorporated in a package—and within a module housing and preferably on a common mount and in thermal contact with a common thermoelectric cooler—of the compact optical module.

While the light sources and optical modules according to the aspects of the invention in this text are primarily described referring to the important application of OCT, they may also advantageously be used for other applications. Such other applications, for example, include Fiber Bragg Interrogators etc.

BRIEF DESCRIPTION OF THE DRAWINGS

In the following, embodiments and aspects of the invention are described referring to drawings. The drawings are all schematic and not to scale, and same reference numerals refer to same or analog elements. The drawings show:

FIG. 7 shows a pictorial view of the optical arrangement with interferometer in an optical module FIGS. 8, 9a, 9b, and 9c depict embodiments of retarding devices;

DESCRIPTION OF THE PREFERRED EMBODIMENTS

Figure 1:
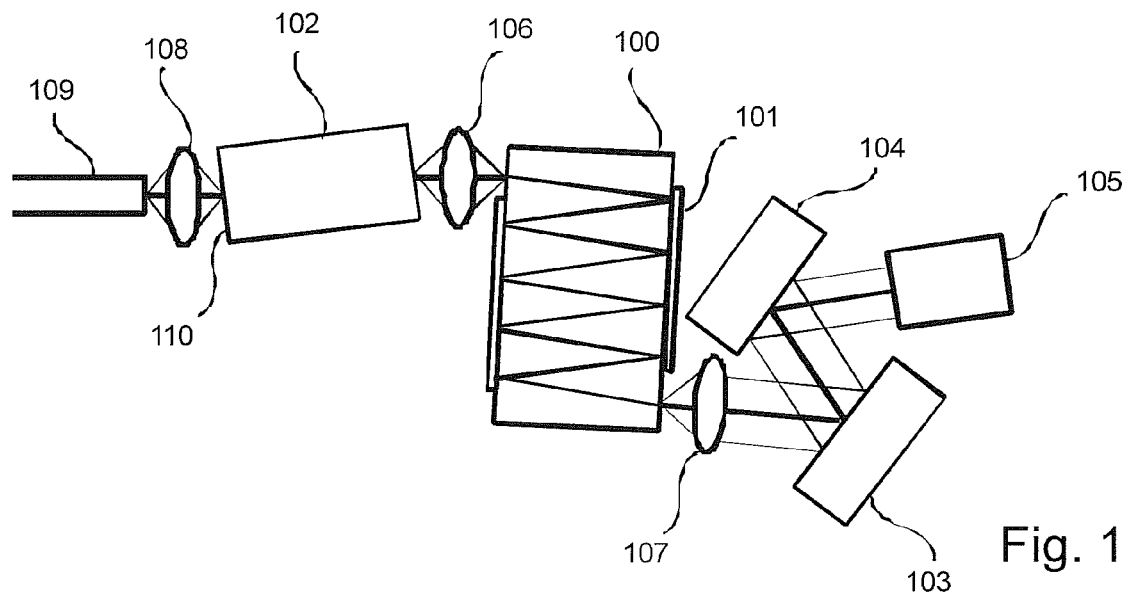
FIG. 1 represents a pictorial view of the optical arrangement using an R-SOA.

A first embodiment of the invention is an optical arrangement as shown in FIG. 1. In this embodiment, the optical arrangement comprises an optical retarding device 100 having reflective coatings 101 at opposing facets, an optical gain block 102, scanning MEMS mirror 103, diffraction grating 104, monitor photodiode 105, a gain block coupling lens 106 and a lens 107 that may be collimating or imaging the beam.

In this embodiment and in other depicted embodiments, the resonator design is based on the so-called Littrow configuration, where the diffraction grating acts as a resonator mirror. However, the invention, pertaining to all embodiments, is not restricted to such configuration. The skilled person will know other resonator configurations of tunable resonators for external cavity diode lasers. Another known configuration is the so-called Littman-Metcalf configuration where a separate mirror (that may be the movable device), onto which diffracted radiation is directed, is used as an end mirror. The skilled person will know ways to re-arrange resonator components in a manner that the grating is not a resonator end mirror.

In this embodiment, the gain block is preferably a reflective-semiconductor optical amplifier (R-SOA) having a broad gain bandwidth of 40-200 nm. The R-SOA has a reflective coating on the face 110 away from the optical retarding device. The optical retarding device 100 is preferably made using a block of, silica, or of glass, polymer, or a semiconductor compound that has mirror layers 101 deposited on its parallel surfaces. The mirror layers are preferably defined such that only parts of the parallel surfaces where the optical beam is retarded are coated. Other parts of the parallel surfaces may be coated with an anti-reflection coating. In FIG. 1, a retarding device is illustrated providing eight reflections in the optical path resulting in nine passes of the retarding device. Alternatively a retarding device can be so used to provide any number of reflections as required for the cavity length of the tunable laser. The optical path in the optical retarding device may optionally be defined by waveguides formed in the block. Such waveguides (this pertains to all embodiments with waveguides in the retarding device block) may have been directly written in the silica, for example by means of a femtosecond pulsed laser.

In another embodiment of the invention the optical retarding device may be made from lithium niobate or any other suitable material.

The optical arrangement forms a tunable external cavity laser of the first above-mentioned type. Light produced in the gain block 102 oscillates in the resonator, defined by the reflective coating 110 on the gain block 102 and the grating 104 (The cavity of the external cavity laser extends between the front facet of the R-SOA 110, that here functions as the outcoupling mirror, and the diffraction grating 104). The lens 107 is used to collimate light between the retarding device 100 and the wavelength selector (that comprises the MEMS mirror 103 and the grating 104, whereas the gain block coupling lens images between the gain block and the optical retarding device. Alternatively, the lens 107 is used to image the light onto the MEMS mirror such that the image size changes between lens 107, MEMS mirror 103 and diffraction grating 104. More in general, any suitable arrangement of imaging and/or collimating means (that may, in addition or as alternative to lenses may include appropriately shaped reflectors) and, if necessary, radiation directing means, may be used. Alternatively to lenses, optical waveguide tapers may be provided by the retarding device to couple light directly to the gain block.

The MEMS mirror used in this embodiment (and other embodiments described herein) preferably scans at frequencies of 20-400 kHz and is driven by either a resonant or linear ramp waveform.

The monitor diode is arranged in a position where it is hit by light portions different from the light portions directed back into the resonator by the grating; for example when the $-1^{st}$ diffraction order is directed back into the resonator, the $1^{st}$ diffraction order or the $0^{th}$ diffraction order may be directed onto the monitor diode 105.

Light from the laser is coupled by a coupling lens 108 into an optical fiber 109.

Figure 2:
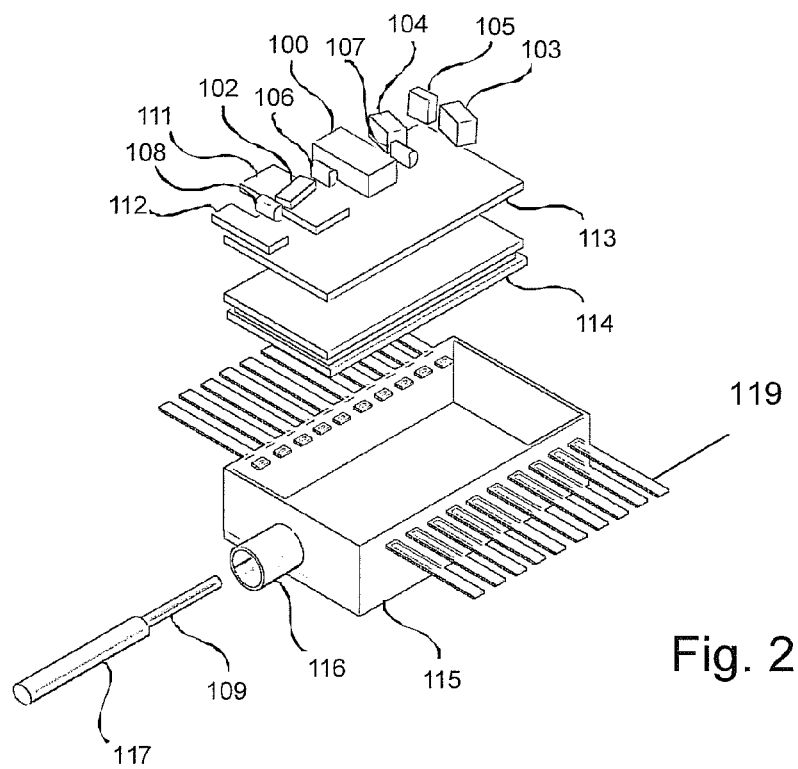
FIG. 2 shows a pictorial view of the assembly of the optical arrangement in an optical module.

FIG. 2 is a view of the assembly of the external tunable laser into a module. Preferably the R-SOA 102 is mounted on a first submount 111 and the fiber 109 is mounted on a second submount 112. Both submounts 111 and 112 are mounted on a carrier 113 (serving as the base) together with the other optical components. The carrier may be mounted on a thermoelectric cooler (TEC) 114 which is itself mounted in an optical module casing 115. The optical module casing may be a butterfly package casing as illustrated in FIG. 2. In another embodiment of the invention, the optical module may be a DIL (dual in line) package or other optical module. The fiber 109 may be fixed to the module feedthrough 116 with a ferule 117. Alternatively the fiber may be fixed to the feedthrough directly. The module comprises also a plurality of electrical feedthroughs 119 for supplying, controlling and tapping the devices in the module.

In another embodiment of the invention, the carrier 113 may be made from two plates whereby a smaller plate is mounted on a larger plate to facilitate mounting of bases of the optical components at different levels to align their optic axes. Alternatively a carrier with different mounting levels machined into its surface may be used.

Figure 3:
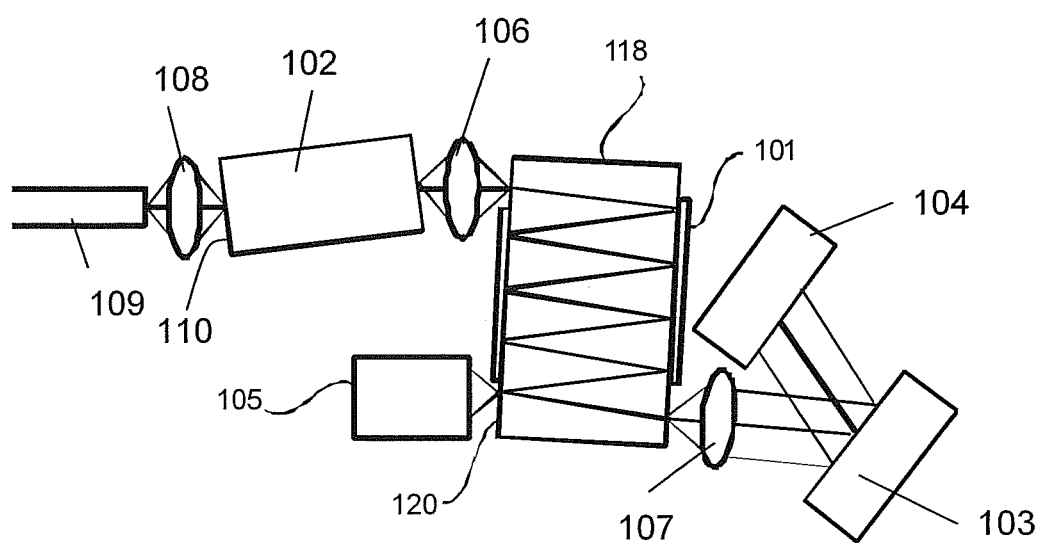
FIG. 3 is a pictorial view of the optical arrangement with monitor diode repositioned.

FIG. 3 illustrates another embodiment of the present invention that is similar to the embodiment of FIG. 1 in that it also corresponds to the first type of arrangements. The elements that have the same function as the ones in FIG. 1 are not explained again here. In the embodiment of FIG. 3, the monitor photodiode 105 is positioned on the same side of the retarding device as the R-SOA 102. In this embodiment, the retarding device 118 is made and positioned so that the optical beam is partially reflected and partially transmitted at one interface so that this may be imaged onto the monitor diode 105. For this embodiment, a partially reflective coating may be used at the part 120 of the face of the retarding device where the optical beam passes through to the monitor diode.

Figure 4:
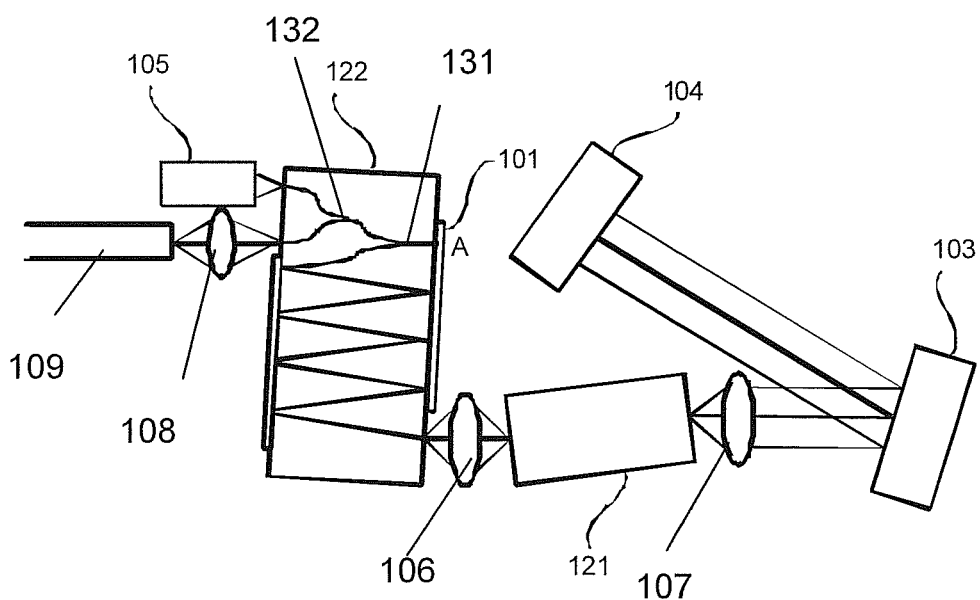
FIG. 4 shows a pictorial view of the optical arrangement using an SOA.
Figure 5:
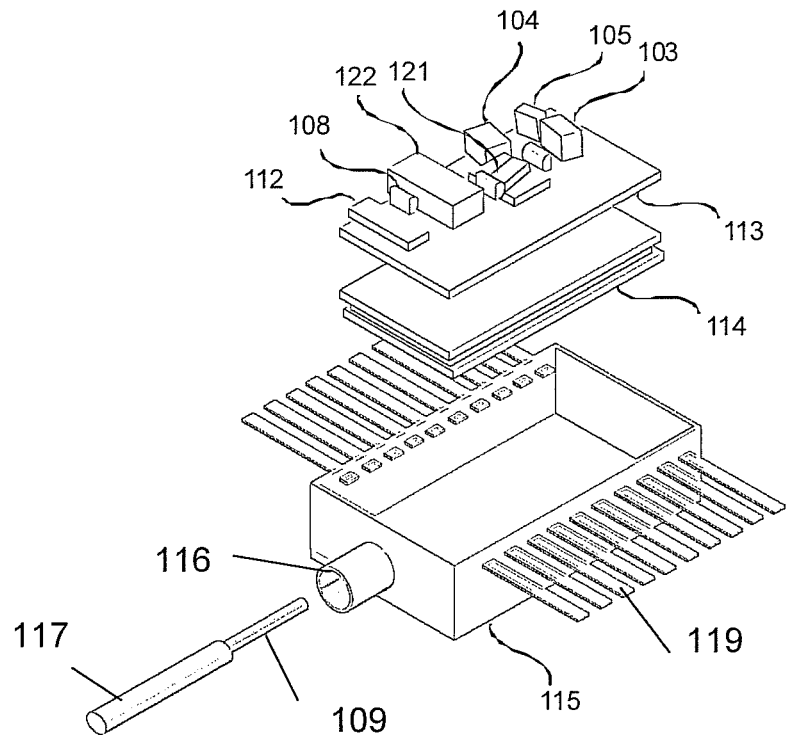
FIG. 5 represents the pictorial view of the assembly of the optical arrangement with SOA in an optical module.

Another arrangement, corresponding to the second type, of the external cavity laser is pictured in FIGS. 4 and 5. This embodiment provides a different retarding device 122, which is positioned to one side of the gain block 121, diffraction grating 104 and MEMS mirror 103. The gain block 121 in this case is a semiconductor optical amplifier (SOA) having anti-reflection coatings on both its facets.

The optical cavity of this arrangement extends from the point A at reflector 101 to the grating 104 (the retarding device is thus passed eight times). In this embodiment, the retarding device is made preferably using waveguides such that light impinges perpendicularly at point A and, for example, also at the outputs of the retarding device 122 to the optical fiber 109 and to the monitor photodiode 105.

Light portions reflected at point A are split between a portion directed back into the resonator and a portion that is directed to the outputs. In the depicted embodiment, this output portion is further split between a portion coupled into the fiber 109 and a portion caused to impinge on the monitor diode.

Here, the splitting between the respective portions is achieved by a first directional coupler 131 (waveguide coupler) and a second directional coupler 132, both formed in the retarding device 122. In an alternative arrangement, the splitting functionality could also be achieved by partially transparent mirrors, for example a partially transparent mirror reflecting back a portion of the radiation into the resonator and coupling out another portion; the monitor diode may then be placed like in FIG. 1 or FIG. 3.

Additionally it is possible to provide a retarding device having optical waveguide tapers to couple light directly to the gain block. It is also possible to provide a retarding device having optical waveguide tapers to couple light directly to optical fiber.

It is possible to use waveguides for only a portion of the beam path in the retarding device, or for the whole beam path in the retarding device.

It is further possible to provide a retarding device where at least a part of the beam path is defined by a waveguide also in arrangements of the first type, for example according to FIG. 1 or according to FIG. 3.

Even further, it would also be possible to provide an arrangement of the second type where the retarding device does not comprise any waveguide, but where the split between the output and light reflected back into the resonator is achieved by other means, such as by a partially transparent mirror.

An advantage of the arrangement shown in FIG. 4 is that the optical power measured by the photodiode is directly proportional to the output power of the external cavity laser.

Figure 6:
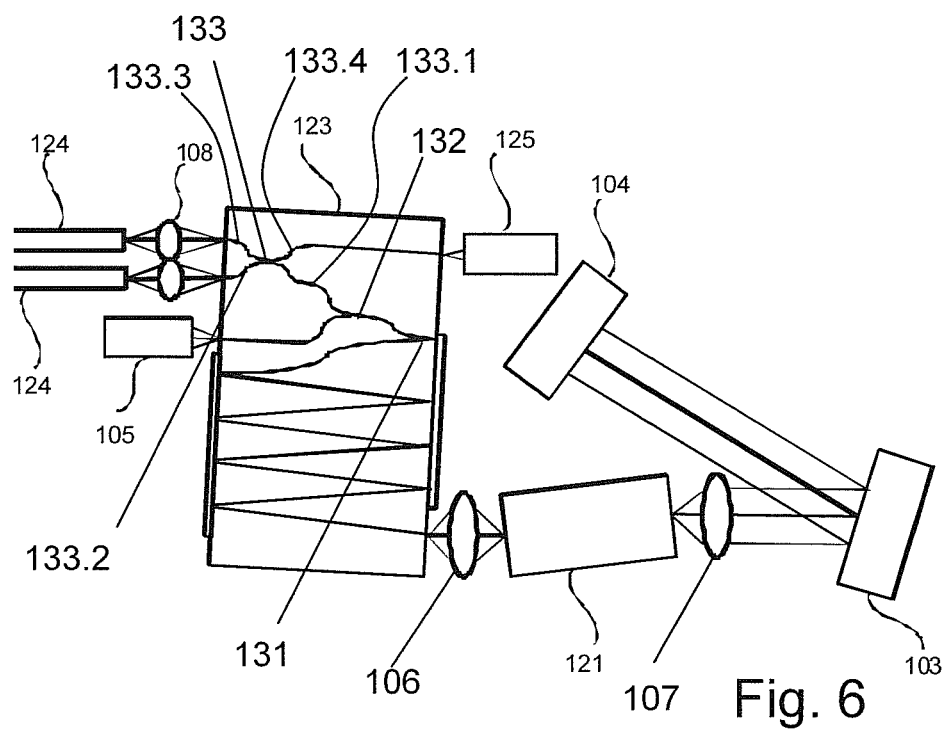
FIG. 6 shows the pictorial view of the optical arrangement using an SOA with integrated interferometer.

FIGS. 6 and 7 show another embodiment of the invention which provides additional optical waveguides in the optical retarding device. Here the retarding device 123 includes a third directional coupler 133 with a first waveguide branch 133.1 (input waveguide) optically-coupled to the external cavity laser and fed by the light coupled out of it, a second and third waveguide branch 133.2, 133.3 (output waveguides) which are optically coupled to two optical fibers 124 and a fourth waveguide branch 133.4 which leads to a reference photodiode 125.

In this embodiment, the third directional coupler 133 has a double function. Firstly, it splits light coming on the input branch 133.1 from the laser to the two output waveguide branches 133.2, 133.3 and thus between the two optical fibers 124 that for example lead to the sample and reference arm of the OCT device, respectively. Secondly, it interferes light coming back from the two fibers 124 via the second and third waveguide branches, respectively. It thus acts as interferometer. The optical fibres act as sample and reference arms of this interferometer which forms part of a Swept Source OCT system, and the reference photodiode 125 for example acts as the detecting device of the OCT system.

This subsystem may be integrated in an optical module having one feedthrough 116 as shown in FIG. 7. Alternatively, the optical module could include a plurality of optical feedthroughs.

In FIGS. 8, 9a, 9b, and 9c, variants of optical retarders that may be used in any embodiment of a multimode swept laser light source that comprises a retarder are depicted. As can be seen in FIGS. 8, 9a, 9b, and 9c, the retarders 100, 118, 122, 123 have plane facets that include facets at an acute or obtuse angle (non-parallel facets at an angle different from 90°) with respect to each other. The facets are mutually arranged—and, in some embodiments, partially provided with the reflective coating 101—so that a beam may impinge on the retarder at a right angle, then be deflected on a well-defined path (with a well-defined number of transitions (passes) through the retarder body and thus having a well-defined length), and then exit the retarder again at a right angle to the exit facet.

Figure 9B:
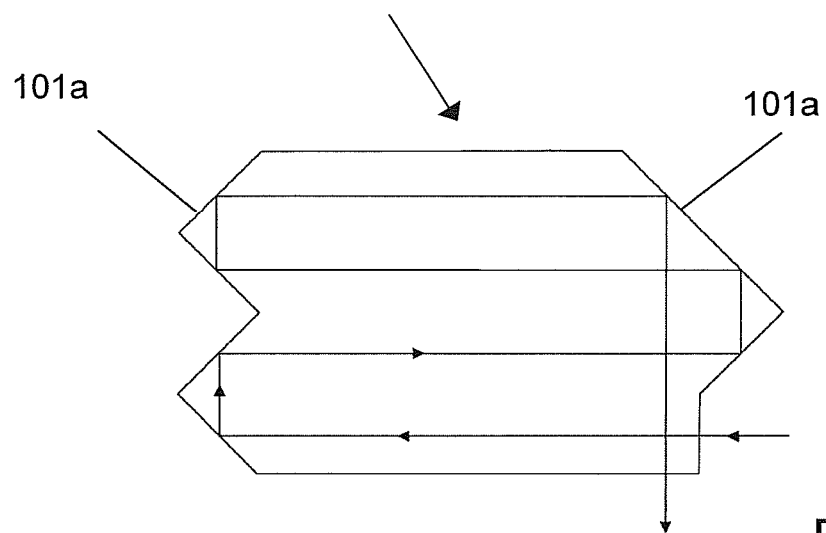
Figure 9C:
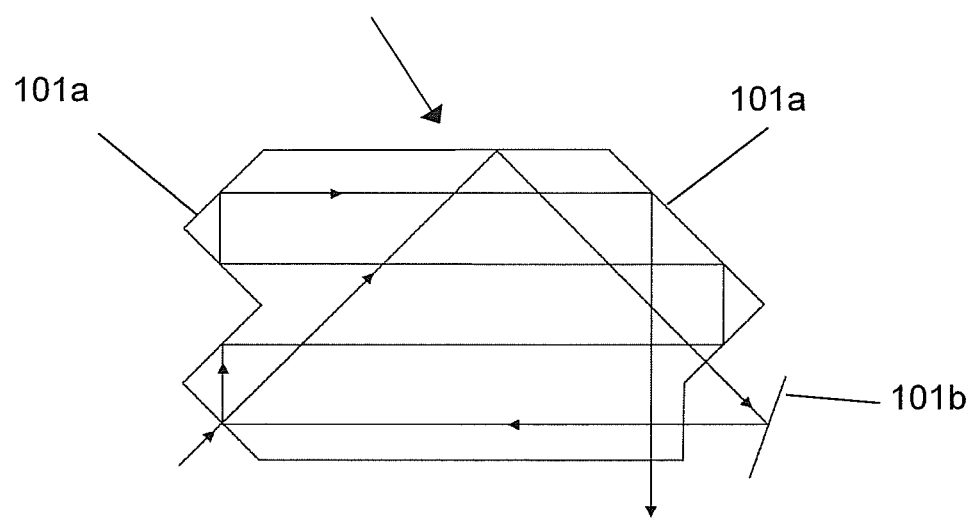

FIGS. 9b and 9c show variants of optical retarders which may be used in any embodiment of a multimode swept laser light source. As can be seen from FIGS. 9b and 9c, these retarders 100, 118, 122, 123 provide multiple-angled facets 101a which are mutually arranged such that a beam may impinge on the retarder at a right angle and then be reflected at each of the angled facets under a low angle. Preferably, the facets are arranged at angles exceeding a critical angle at which an incoming beam is totally internally reflected. The facets 101a may be defined with or without high-reflectivity coatings. The retarder depicted in FIG. 9c may be used together with an external reflector 101b such that a beam enters and leaves the retarder more than once, every time preferably at a right angle.

The skilled person will realize that the concept of having a body with more than six plane facets that include facets at an acute angle will, by application of geometrical optics, yield a plurality of further variants of retarder shapes that all ensure right entrance and exit angles in combination with a well-defined number of transitions through the body.

Figure 10:
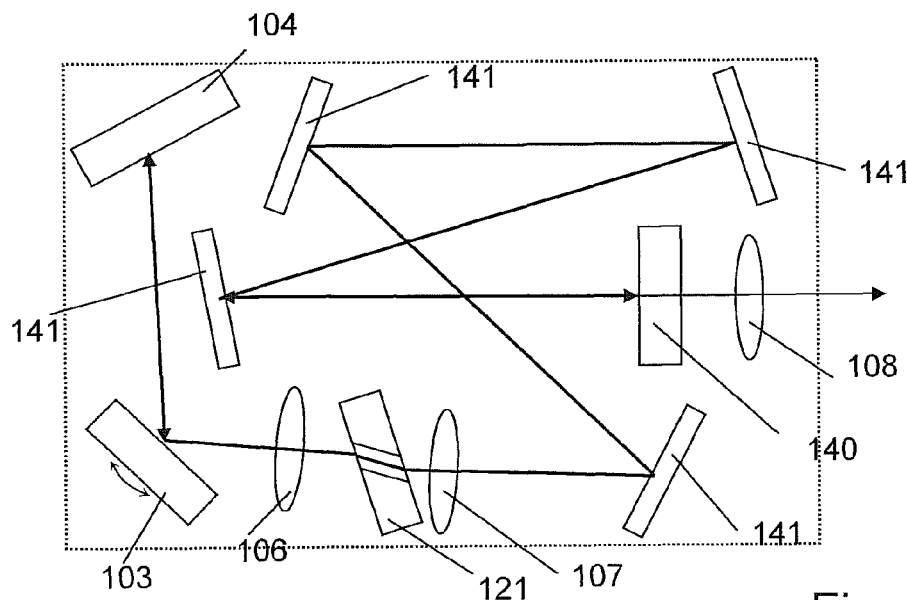
FIG. 10 shows an embodiment of a light source according to the first aspect of the invention without a retarding device.

FIG. 10 shows a variant of a multimode external cavity swept laser light source that comprises, in an optical module casing, a gain device 121, a wavelength selector 103, 104 and light re-directors 104, 106, 107. In contrast to the hereinbefore-described embodiments, the resonator does not comprise an optical retarder but is folded to have a sufficient cavity length corresponding to a plurality of module lengths.

In the depicted embodiment, the gain device 121 is an SOA, thus a gain block where neither of the facets reflects light back into the device. For example, the facets may be at a non-perpendicular angle to the beam direction and/or the facets may comprise AR coatings, etc.

However, it would also be possible to provide a light source without a retarder of the kind shown in FIG. 10 with an RSOA gain element, for example at the position of the outcoupling mirror 140. The advantage would be the same as for devices with optical retarder: the reduction of coupling losses.

Figure 11:
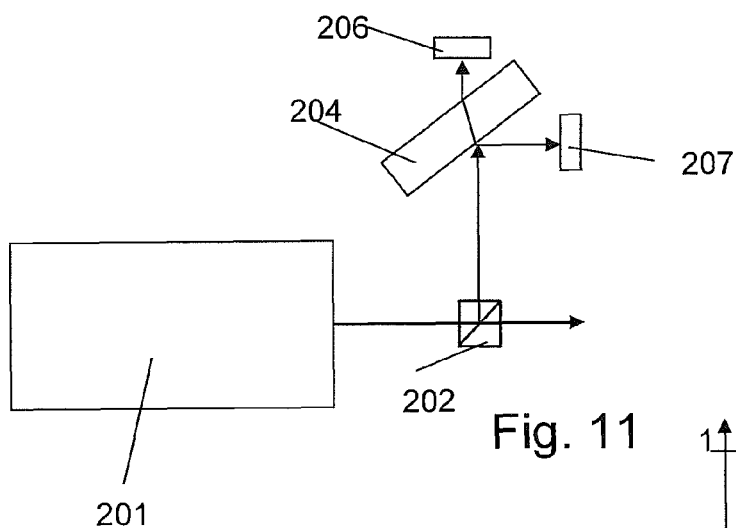
FIG. 11 shows an optical module with a wavemeter according to the third aspect of the invention.
Figure 12:
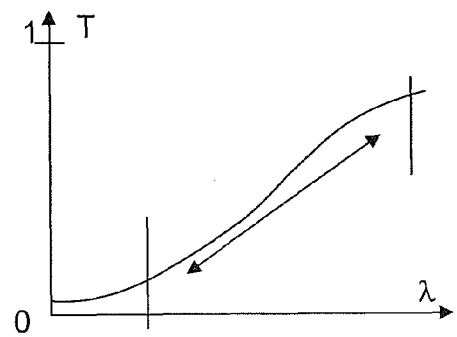
FIG. 12 depicts a schematical representation of a wavelength dependent filter transmission characteristic.
Figure 13:
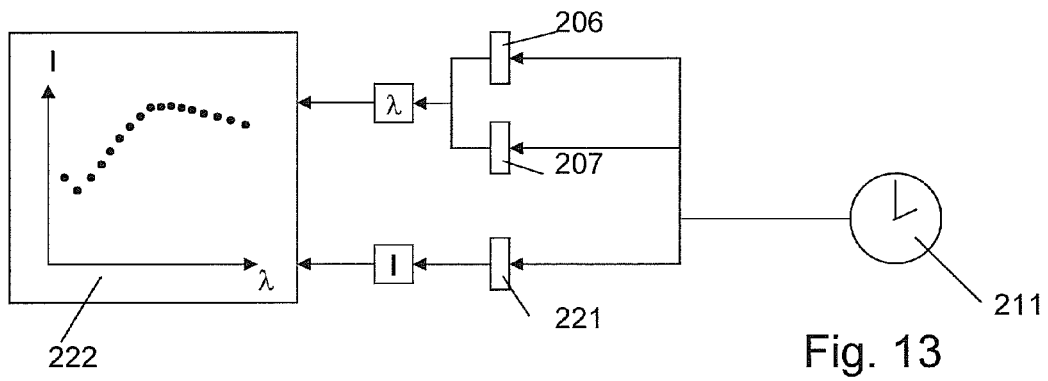
FIG. 13 shows a scheme of an optical module according to the third aspect.

Referring to FIGS. 11, 12 and 13, a concept of a wavemeter of a swept light source according to the third aspect of the invention is described. In analizing data obtained by measurement devices with swept light sources, it is in most cases important to know which data point corresponds to which wavelength of light produced by the swept source. In prior art Optical Coherence Tomography (OCT) devices—and similar devices—therefore, a so-called k-clock is used for data sampling. The letter 'k' in this is used to refer to the wavenumber k that is proportional to the inverse of the wavelength and, in a given medium, is thus proportional to the frequency. The k-clock of prior art devices comprises a Fabry-Perot filter or the like through which a portion of the generated light is directed. The signal transmitted through the filter will have a characteristic dependency on the frequency with a pattern of peeks in regular frequency distances of, for example, 25 GHz. The peeks are then used to trigger sampling of the actual signal. This way to proceed has two disadvantages. Firstly, the absolute wavelength position is not known but only the relative peek-to-peek distance. Secondly, the peek-to-peek frequency distance—the free spectral range of the Fabry-Perot filter—is fixed. However, given a usually non-linear output-frequency—time relationship, the sampling will be at irregular time intervals, and this produces non-trivial synchronization problems.

FIG. 11 depicts a wavemeter of a device according to the third aspect of the invention. The block 201 denotes the swept light source, which may be a light source according to one or both of the hereinbefore described aspects of the invention. Although the light source 201 is shown in this figure and in subsequent figures as block separate from the further elements, in practice also the further elements can be integrated in the package that comprises the light source, and the further elements can be arranged physically between elements of the light source (but not, of course, interrupting the beam path within the resonator of the light source) or in separate positions. By means of a beam splitter 202 a portion—for example between 1% and 10% of the beam is 'tapped', i.e. directed away from the main beam and onto the wavemeter.

The wavemeter comprises a filter device 204 on which the tapped beam portion impinges. The filter in the depicted embodiment is a bandpass filter, the passband of which is offset relative to the wavelength range, so that the wavelength range is in a sloped portion of the filter transmission characteristics.

FIG. 12 shows a schematic dependence of a relative filter transmission power (intensity transmission coefficient) on the wavelength. The vertical lines schematically depict the upper and lower limits of the wavelength range.

Returning to FIG. 11, in addition to the filter device 204, the wavemeter comprises a first light intensity detector 206 and a second light intensity detector 207. The first light intensity detector is configured and arranged to detect light of the tapped beam that is transmitted through the filter. The second light intensity detector 207 is configured and arranged to detect light portions that are not transmitted by the filter 204 and are consequently reflected by it.

Because of the dependence of the transmitted intensity on the wavelength, the quantity $I_T-I_R$ being the difference between the intensity $I_T$ measured by the first light intensity detector 206 and the intensity $I_R$ measured by the second light intensity detector 207 is a measure of the wavelength. Preferably, the normalized value $(I_T-I_R)/(I_T+I_R)$ is used as an input quantity for determining, using the known filter characteristics, the wavelength. The filter characteristic can be, based on an initial measurement, for example by the manufacturer, stored in the device's electronics. It would also be possible to use the quantity $(I_T-I_R)/(I_T+I_R)$ itself as a measure of the wavelength.

Because of this approach, the absolute value of the wavelength is known, and not only a relative measure. Further, the measurement of the wavelength values can be done at any time, i.e. with any sampling rate set by a separate clock. Thus, it is possible to use the system clock or another clock in time with such a system clock. Synchronization of the device is much easier than in prior art approaches where the signal peeks of the k-clock itself had to serve as synchronizing signal.

FIG. 13 very schematically illustrates an according measurement system. The system clock 211 provides a trigger signal for reading out the measurement values of the first and second wavemeter intensity detectors 206, 207 as well as of the wanted signal intensity detector 221. The system electronics calculates the wavelength from the wavemeter intensity detector signals and stores the intensity/wavelength data pairs; these values may be displayed and/or used in further calculations as known in the art. In reality, for each detector an analog/digital converter triggered by the trigger signal may be used to read out the signals. Also, the clock trigger signal may be used also for sampling further signals, and/or the wanted signal may be obtained from a plurality of detector signals, as for example in the embodiment described hereinafter.

Figure 14:
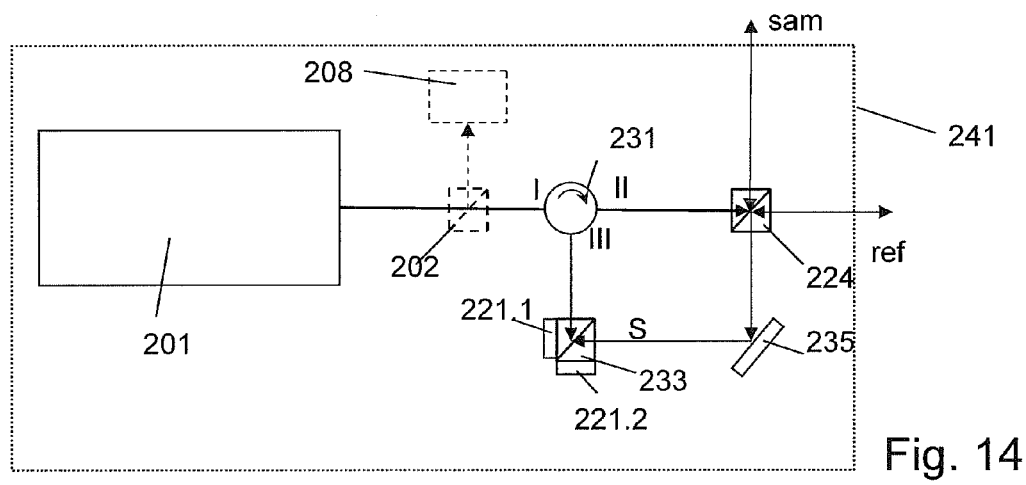
FIG. 14 depicts an optical module with a DC offset compensation.

FIG. 14 shows a measurement principle that may be used to compensate a DC offset that may result from fluctuations of the light source intensity or of measurement parameters. The set-up is based on the principle of 'balanced detection'. In the depicted embodiment, a circulator 231 is used to direct the light portion coming back as a second output of the beam splitter/combiner 224 (to port II of the circulator) to a balanced detector where it is combined with the wanted signal S to interfere. In the depicted embodiment, the wanted signal S is an OCT signal obtained from interfering a signal combing back from a sample path sam and a signal coming back from a reference path ref. In the depicted embodiment, a beam splitter/combiner 224 is used to split the main beam between the sample path and the reference path and to combine them together to interfere. A deflector 235 is used to direct the signal beam onto a combiner 233 and two intensity detectors 221.1, 221.2. The intensity difference measured at the two detectors 221.1, 221.2 is used as the balanced signal. The circulator is operable to direct light entering port I to port II, light entering port II to port III, and light coming from port III to port I. In addition to serving to direct a second output of the beam splitter/combiner to the balanced detection set-up, it also serves as an optical isolator keeping light from being fed back to the laser light source.

In FIG. 14, the—optional wavemeter 208 of the kind described referring to FIGS. 11-13 is illustrated by dashed lines.

Figure 15:
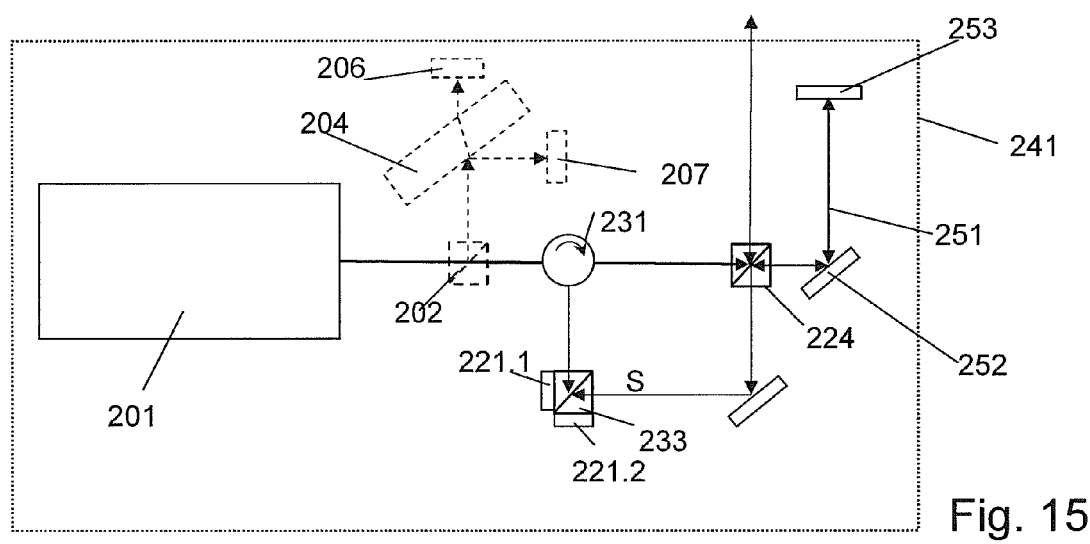
FIG. 15 shows an optical module with a reference arm.

The optical module shown in FIG. 14 and comprising the light source 201 as well as the optical components of the wavemeter 208 (if present), of the beam splitter/combiner and the intensity detectors as well as potential beam directing means, may comprise a module casing in which the optical module components are arranged, the module casing comprising optical and electrical feedthroughs, like the devices illustrated in FIGS. 2, 5, 7. The optical module components may be arranged on a common mount in contact with a common module thermoelectric cooler. FIG. 15 depicts an optical module for an OCT device. The optical module comprises, preferably within a single module housing with feedthroughs and possibly with a common mount on a common cooler, in addition to the light source 201, the (optional) optical components of the wavemeter and the intensity detector(s)—in the depicted embodiment, two intensity detectors and a DC offset compensation arrangement as described hereinbefore are illustrated—the optical module also comprises the reference arm 251 of the OCT. The reference arm will comprise light deflecting and/or light guiding means 252, 253 that direct the reference light beam from the beam splitter/combiner 224 on an optical path with a defined optical length back to the beam splitter/combiner 224. The embodiment of FIG. 15—as well as an according variant of a dual beam swept source optical module as described further below but with an integrated reference arm—is advantageous because of its compactness in cases the overall OCT device is small, for example in a hand-held device where the distance to the measured object is small.

Figure 16:
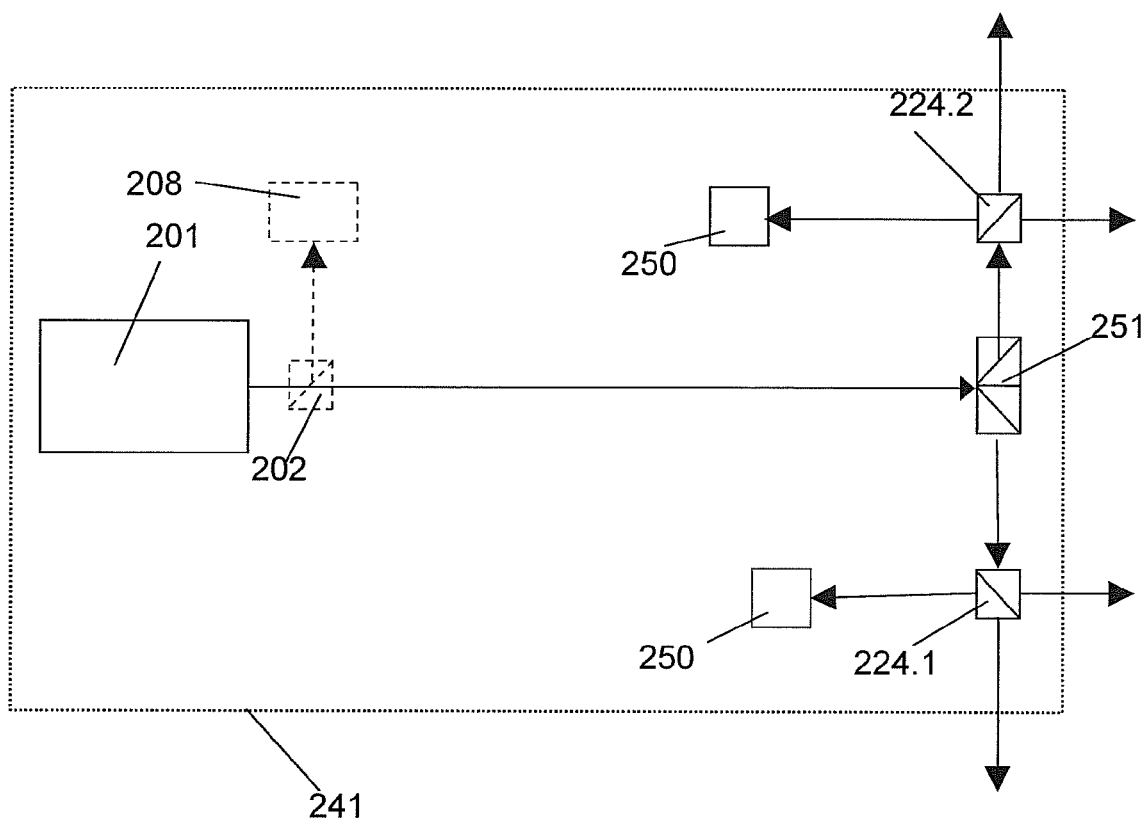
FIG. 16 depicts a dual beam OCT module.

FIG. 16 yet depicts a dual beam swept source optical module for an OCT device. The dual beam swept source optical module comprises a single swept laser light source 201, preferably of the kind described as previous embodiments. The optical module may further comprise a wavemeter 202, 208 of the above-described kind. Preferably downstream of the wavemeter (i.e. arranged after the wavemeter in a primary beam path) a beam splitter 251 is positioned to split the primary beam into two partial beams, for example in a ratio of about 50:50. The two partial beams are used for individual OCT measurement of two separate OCT device branches. For example, the two branches may be used to make an OCT image of the left and right eye, respectively. The OCT device then may be made as a kind of binocular-like device.

Each partial beam is directed onto a beam splitter/combiner 224.1, 224.2, and from there partial beam portions are directed on a sample arm and a reference arm, respectively. The reference arm may be within the optical module or, as depicted, comprise portions outside of the optical module. Light of the respective sample arm and the reference arm coming back to the beam splitter/combiners 224.1, 224.2 is brought to interfere, and then the intensity is measured in both branches individually. Optionally, the branches may each comprise an intensity reference set-up as described referring to FIG. 14. To that end, for each branch a portion of the light produced by the light source 201 is tapped (beam splitting taps for directing a small portion away are denoted by 231.1 and 232.2 in FIG. 16), and the intensity detecting means of each branch comprise two intensity detectors 221.1, 221.2; 221.3, 221.4. The tapping of the light portion from the primary beam may be upstream of the beam splitter (as illustrated) or also in each branch downstream of the beam splitter.

In FIG. 16, reference number 250 schematically depicts a detection scheme. Also in FIG. 16—like in all other embodiments—the detection may be based on a balanced heterodyne detection scheme that includes. To this end, an optical circulator may, for example, be present between the beam splitter 251 and each of the beam splitter/combiners 224,1, 224.2.

Also in the embodiment of FIG. 16, the components illustrated to be within the casing 241 (that has optical and electrical feedthroughs just like in the previously described embodiments) may be on a common mount and may be in thermal contact with a common thermoelectric cooler.

In all embodiments that comprise both, a tap for the wavemeter and at least one tap for the intensity reference, the sequence of the taps with respect to a primary beam path may be reversed compared to the described embodiments.

In all embodiments, the monitor (if present) and/or the detector(s) (if present) need not necessarily be photodiodes, but may be other suitable detectors for detecting light intensities.

In the embodiments that integrate a part of an interferometer inside the optical module (such as the embodiments depicted in FIGS. 6, and 14-16), it may be advantageous to provide an optical isolator. In such embodiments, absent an optical isolator, reflections from the sample and reference arm might travel back into the swept source laser. The optical circulators of the embodiments having a balanced detection scheme serves as such an optical isolator by keeping light incident on port II from being transmitted to port III. For embodiments that do not have the optical circulator, or in addition thereto, depending on the power level of those reflections it might be advisable to also integrate an optical isolator in order to protect the swept source laser. The optical isolator would be placed, for example, in between the light source 201 and the beam splitter/combiner 224. An optical isolator may, like an optical circulator, be based on the Faraday rotator principle.

It would be possible to provide the functionalities of the optical modules described referring to FIGS. 11-16 also using waveguide technology, for example in a photonic light wave circuit PLC.

While many embodiments of the invention are described herein, it will be understood by those skilled in the art that changes may be made without departing from the spirit and scope of the invention as defined by the appended claims.

What is claimed is:

1. A light source, comprising:
   a semiconductor gain device;
   an optical retarding device, the retarding device comprising a block of material, a beam path with a well-defined beam path length being defined for light within the block of material produced by the gain device;
   a wavelength selector; and
   a base;
   the gain device, the retarding device and wavelength selector being mutually arranged on the base so that a resonator is established for light portions emitted by the gain device and selected by the wavelength selector;
   wherein the beam path in the retarding device is a part of a beam path of the resonator and
   wherein the optical beam path length in the retarding device constitutes at least 30% of optical resonator length.

2. The light source according to claim 1, wherein the retarding device comprises a plurality of reflective surfaces for reflecting back and forth light portions propagating in the block of material.

3. The light source according to claim 2, wherein the retarding device defines at least four reflections of the beam path at the reflective surfaces.

4. The light source according to claim 1, wherein the beam path within the retarding device is at least partially defined by a waveguide.

5. A light source, comprising:
   a semiconductor gain device;
   an optical retarding device, the retarding device comprising a block of material, a beam path with a well-defined beam path length being defined for light within the block of material produced by the gain device;
   a wavelength selector; and
   a base;
   the gain device, the retarding device and wavelength selector being mutually arranged on the base so that a resonator is established for light portions emitted by the gain device and selected by the wavelength selector;
   wherein the beam path in the retarding device is a part of a beam path of the resonator and
   wherein the retarding device has a plurality of plane facets that include facets that are at an acute angle with respect to each other, wherein at least two of the facets are at least partially reflective and reflect light impinging on the facet from an inside of the body back into the body, and wherein the body is designed and arranged in the resonator so that the light path in the resonator is perpendicular to non-reflective entrance and exit end facets and is non-perpendicular to reflective facet portions upon which it impinges.

6. A light source, comprising:
   a semiconductor gain device;
   an optical retarding device, the retarding device comprising a block of material, a beam path with a well-defined beam path length being defined for light within the block of material produced by the gain device;
   a wavelength selector; and
   a base;
   the gain device, the retarding device and wavelength selector being mutually arranged on the base so that a resonator is established for light portions emitted by the gain device and selected by the wavelength selector;
   wherein the beam path in the retarding device is a part of a beam path of the resonator and
   wherein the retarding device comprises at least one directional coupler,
   further comprising two waveguide outputs and further comprising a detector, wherein the at least one directional coupler is arranged to bring light portions coming back from the two waveguide outputs into interference and to direct interfered light portions onto the detector.

7. The light source according to claim 1, further comprising a monitor.

8. The light source according to claim 1, wherein the wavelength selector comprises a MEMS movable device.

9. The light source according to claim 1, wherein the wavelength selector comprises a MEMS mirror and a diffraction grating, the MEMS mirror is configured for scanning an incident angle of a light beam on the diffraction grating, or wherein the wavelength selector comprises an integrated MEMS grating-mirror device.

10. The light source according to claim 9, wherein the diffraction grating or the integrated MEMS grating-mirror device, respectively, defines an end face of the resonator.

11. The light source according to claim 1, wherein the semiconductor gain device is chosen from a group comprising a semiconductor amplifier and a reflective semiconductor amplifier.

12. The light source according to claim 1, further comprising an optical fiber optically coupled to an output of the resonator.

13. The light source according to claim 1, further comprising a thermoelectric cooler connected and thermally coupled to the base.

14. The light source according to claim 1, further comprising an optical package casing encasing the gain device, the retarding device, the wavelength selector, and the base, the package casing comprising at least one optical feedthrough and a plurality of electrical feedthroughs.

15. An optical module comprising, a light source according to claim 1 in an optical module casing, and an electronics unit capable of controlling the light source and/or of analyzing a signal from a detecting means of the optical module.

16. The optical module according to claim 15, further comprising a wavemeter, the wavemeter comprising:
   a wavemeter tap capable of directing a wavemeter portion of light produced by the light source away from a main beam,
   a wavelength selective filter arranged to receive the wavemeter portion,
   a first wavemeter detector arranged to measure a transmitted radiation intensity of radiation transmitted through the filter, and
   a second wavemeter detector arranged to measure a non-transmitted radiation intensity of radiation not transmitted through the filter,
   wherein the wavemeter tap, the wavelength selective filter, the first wavemeter detector and the second wavemeter detector are preferably arranged in the module casing.

17. The optical module according to claim 16, wherein the electronics unit is equipped for comparing and analyzing signals of the first and second wavemeter detectors, wherein the electronics unit is equipped for analysis of the signals via evaluating the value (IT IR)/(IT+IR), where IT is the intensity measured by the first light intensity detector and IR is the intensity measured by the second light intensity detector.

18. The optical module according to claim 15, further comprising a DC signal offset compensation based on balanced heterodyne detection.

19. The optical module according to claim 15, further comprising a beam splitter/combiner and a desired signal intensity detector, the beam-splitter/combiner being provided for splitting a primary beam between a sample arm and a reference arm and for combining light portions coming back from the sample arm and the reference arm and for directing combined, interfering light portions onto the desired signal intensity detector.

20. The optical module according to claim 19, further comprising, within the module casing, a reference arm with light deflecting and/or light guiding means that direct the reference light beam from the beam splitter/combiner on an optical path with a defined optical length back to the beam splitter/combiner.

21. The optical module according to claim 15, further comprising a primary beam splitter for splitting the primary beam into two partial beams, and, for each partial beam path including a beam splitter/combiner and a desired signal intensity detector, each beam splitter/combiner being provided for splitting the respective partial beam path between a sample arm and a reference arm and for combining light portions coming back from the sample arm and the reference arm and for directing combined, interfering light portions onto the respective desired signal intensity detector.

22. An optical coherence tomography apparatus, comprising:
a light source according to claim 1;
at least a portion of an interferometer in optical communication with the light source;
an optics unit, the optics unit suitable for focusinq a light portion originating from the light source onto a chosen location of a sample, and of performing a scan, in which said location and the sample are moved relative to one another;
the interferometer being provided for combining a portion of light produced by the light source and returned from the sample with a portion of light produced by the light source and returned to the interferometer via a reference path; and
a detector unit positioned to receive combined light from the interferometer.

23. The apparatus according to claim 22, wherein the portion of the interferometer and the detector unit are mounted within the optical module casing.

24. An optical coherence tomography module for an optical coherence tomography apparatus, the module comprising:
a light source according to claim 1;
a portion of an interferometer in optical communication with the light source and operable to combine a portion of light produced by the light source and returned from a sample with a portion of light produced by the light source and returned from a reference path; and
a detector unit positioned to receive combined light from the interferometer.

25. The module according to claim 24, wherein the portion of the interferometer and the detector unit are mounted within the optical module casing.

26. The apparatus according to claim 24, wherein the resonator comprises the optical retarding device, the retarding device comprising a block of material, a beam path with a well-defined beam path length within the block of material being defined for light produced by the gain device.

27. The light source according to claim 1, wherein the retarding device has a plurality of plane facets that include facets that are at an acute angle with respect to each other, wherein at least two of the facets are at least partially reflective and reflect light impinging on the facet from an inside of the body back into the body, and wherein the body is designed and arranged in the resonator so that the light path in the resonator is perpendicular to non-reflective entrance and exit end facets and is non-perpendicular to reflective facet portions upon which it impinges.

28. The light source according to claim 1, wherein the retarding device comprises at least one directional coupler, the light source further comprising two waveguide outputs and further comprising a detector, wherein the at least one directional coupler is arranged to bring light portions coming back from the two waveguide outputs into interference and to direct interfered light portions onto the detector.

29. The light source according to claim 6, wherein the retarding device has a plurality of plane facets that include facets that are at an acute angle with respect to each other, wherein at least two of the facets are at least partially reflective and reflect light impinging on the facet from an inside of the body back into the body, and wherein the body is designed and arranged in the resonator so that the light path in the resonator is perpendicular to non-reflective entrance and exit end facets and is non-perpendicular to reflective facet portions upon which it impinges.

30. The light source according to claim 5, wherein the retarding device comprises a plurality of reflective surfaces for reflecting back and forth light portions propagating in the block of material.

31. The light source according to claim 30, wherein the retarding device defines at least four reflections of the beam path at the reflective surfaces.

32. The light source according to claim 1, wherein the semiconductor gain device is configured for providing light amplification.

33. The light source according to claim 5, wherein the semiconductor gain device is configured for providing light amplification.

34. The light source according to claim 6, wherein the semiconductor gain device is configured for providing light amplification.

35. The light source according to claim 5, further comprising a monitor.

36. The light source according to claim 6, further comprising a monitor.

37. The light source according to claim 5, wherein the wavelength selector comprises a MEMS movable device.

38. The light source according to claim 6, wherein the wavelength selector comprises a MEMS movable device.

39. The light source according to claim 5, wherein the wavelength selector comprises a MEMS mirror and a diffraction grating, the MEMS mirror configured for scanning an incident angle of a light beam on the diffraction grating, or wherein the wavelength selector comprises an integrated MEMS grating-mirror device.

40. The light source according to claim 6, wherein the wavelength selector comprises a MEMS mirror and a diffraction grating, the MEMS mirror configured for scanning an incident angle of a light beam on the diffraction grating, or wherein the wavelength selector comprises an integrated MEMS grating-mirror device.

41. The light source according to claim 39, wherein the diffraction grating or the integrated MEMS grating-mirror device, respectively, defines an end face of the resonator.

42. The light source according to claim 40, wherein the diffraction grating or the integrated MEMS grating-mirror device, respectively, defines an end face of the resonator.

43. The light source according to claim 5, wherein the semiconductor gain device is chosen from a group comprising a semiconductor amplifier and a reflective semiconductor amplifier.

44. The light source according to claim 6, wherein the semiconductor gain device is chosen from a group comprising a semiconductor amplifier and a reflective semiconductor amplifier.

45. The light source according to claim 5, further comprising an optical fiber optically coupled to an output of the resonator.

46. The light source according to claim 6, further comprising an optical fiber optically coupled to an output of the resonator.

47. The light source according to claim 5, further comprising a thermoelectric cooler connected and thermally coupled to the base.

48. The light source according to claim 6, further comprising a thermoelectric cooler connected and thermally coupled to the base.

49. The light source according to claim 5, further comprising an optical package casing encasing the gain device, the retarding device, the wavelength selector, and the base, the package casing comprising at least one optical feedthrough and a plurality of electrical feedthroughs.

50. The light source according to claim 6, further comprising an optical package casing encasing the gain device, the retarding device, the wavelength selector, and the base, the package casing comprising at least one optical feedthrough and a plurality of electrical feedthroughs.

51. An optical module comprising, a light source according to claim 5 in an optical module casing, and an electronics unit capable of controlling the light source and/or of analyzing a signal from a detecting means of the optical module.

52. An optical module comprising, a light source according to claim 6 in an optical module casing, and an electronics unit capable of controlling the light source and/or of analyzing a signal from a detecting means of the optical module.

53. The optical module according to claim 51, further comprising a wavemeter, the wavemeter comprising:
- a wavemeter tap capable of directing a wavemeter portion of light produced by the light source away from a main beam, a
- wavelength selective filter arranged to receive the wavemeter portion,
- a first wavemeter detector arranged to measure a transmitted radiation intensity of radiation transmitted through the filter, and
- a second wavemeter detector arranged to measure a non-transmitted radiation intensity of radiation not transmitted through the filter,
- wherein the wavemeter tap, the wavelength selective filter, the first wavemeter detector and the second wavemeter detector are preferably arranged in the module casing.

54. The optical module according to claim 52, further comprising a wavemeter, the wavemeter comprising:
- a wavemeter tap capable of directing a wavemeter portion of light produced by the light source away from a main beam,
- a wavelength selective filter arranged to receive the wavemeter portion,
- a first wavemeter detector arranged to measure a transmitted radiation intensity of radiation transmitted through the filter, and
- a second wavemeter detector arranged to measure a non-transmitted radiation intensity of radiation not transmitted through the filter,
- wherein the wavemeter tap, the wavelength selective filter, the first wavemeter detector and the second wavemeter detector are preferably arranged in the module casing.

55. The optical module according to claim 53, wherein the electronics unit is equipped for comparing and analyzing signals of the first and second wavemeter detectors, wherein the electronics unit is equipped for analysis of the signals via evaluating the value (IT IR)/(IT+IR), where IT is the intensity measured by the first light intensity detector and IR is the intensity measured by the second light intensity detector.

56. The optical module according to claim 54, wherein the electronics unit is equipped for comparing and analyzing signals of the first and second wavemeter detectors, wherein the electronics unit is equipped for analysis of the signals via evaluating the value (IT IR)/(IT+IR), where IT is the intensity measured by the first light intensity detector and IR is the intensity measured by the second light intensity detector.

57. The optical module according to claim 51, further comprising a DC signal offset compensation based on balanced heterodyne detection.

58. The optical module according to claim 52, further comprising a DC signal offset compensation based on balanced heterodyne detection.

59. The optical module according to claim 51, further comprising a beam splitter/combiner and a desired signal intensity detector, the beam-splitter/combiner being provided for splitting a primary beam between a sample arm and a reference arm and for combining light portions coming back from the sample arm and the reference arm and for directing combined, interfering light portions onto the desired signal intensity detector.

60. The optical module according to claim 52, further comprising a beam splitter/combiner and a desired signal intensity detector, the beam-splitter/combiner being provided for splitting a primary beam between a sample arm and a reference arm and for combining light portions coming back from the sample arm and the reference arm and for directing combined, interfering light portions onto the desired signal intensity detector.

61. The optical module according to claim 59, further comprising, within the module casing, a reference arm with light deflecting and/or light guiding means that direct the reference light beam from the beam splitter/combiner on an optical path with a defined optical length back to the beam splitter/combiner.

62. The optical module according to claim 60, further comprising, within the module casing, a reference arm with light deflecting and/or light guiding means that direct the reference light beam from the beam splitter/combiner on an optical path with a defined optical length back to the beam splitter/combiner.

63. The optical module according to claim 51, further comprising a primary beam splitter for splitting the primary beam into two partial beams, and, for each partial beam path including a beam splitter/combiner and a desired signal intensity detector, each beam splitter/combiner being provided for splitting the respective partial beam path between a sample arm and a reference arm and for combining light portions coming back from the sample arm and the reference arm and for directing combined, interfering light portions onto the respective desired signal intensity detector.

64. The optical module according to claim 52, further comprising a primary beam splitter for splitting the primary beam into two partial beams, and, for each partial beam path including a beam splitter/combiner and a desired signal intensity detector, each beam splitter/combiner being provided for splitting the respective partial beam path between a sample arm and a reference arm and for combining light portions coming back from the sample arm and the reference arm and for directing combined, interfering light portions onto the respective desired signal intensity detector.

65. An optical coherence tomography apparatus comprising:
- a light source according to claim 5;
- at least a portion of an interferometer in optical communication with the light source;
- an optics unit, the optics unit suitable for focusing a light portion originating from the light source onto a chosen location of a sample, and of performing a scan, in which said location and the sample are moved relative to one another;
- the interferometer being provided for combining a portion of light produced by the light source and returned from the sample with a portion of light produced by the light source and returned to the interferometer via a reference path; and a detector unit positioned to receive combined light from the interferometer.

66. An optical coherence tomography apparatus comprising:
a light source according to claim 6;
at least a portion of an interferometer in optical communication with the light source;
an optics unit, the optics unit suitable for focusing a light portion originating from the light source onto a chosen location of a sample, and of performing a scan, in which said location and the sample are moved relative to one another;
the interferometer being provided for combining a portion of light produced by the light source and returned from the sample with a portion of light produced by the light source and returned to the interferometer via a reference path; and
a detector unit positioned to receive combined light from the interferometer.

67. The optical coherence tomography apparatus according to claim 65, wherein the portion of the interferometer and the detector unit are mounted within the optical module casing.

68. The optical coherence tomography apparatus according to claim 66, wherein the portion of the interferometer and the detector unit are mounted within the optical module casing.

69. An optical coherence tomography module for an optical coherence tomography apparatus, the module comprising:
a light source according to claim 5;
a portion of an interferometer in optical communication with the light source and operable to combine a portion of light produced by the light source and returned from a sample with a portion of light produced by the light source and returned from a reference path; and
a detector unit positioned to receive combined light from the interferometer.

70. An optical coherence tomography module for an optical coherence tomography apparatus, the module comprising:
a light source according to claim 6;
a portion of an interferometer in optical communication with the light source and operable to combine a portion of light produced by the light source and returned from a sample with a portion of light produced by the light source and returned from a reference path; and
a detector unit positioned to receive combined light from the interferometer.

71. The optical coherence tomography module according to claim 69, wherein the portion of the interferometer and the detector unit are mounted within the optical module casing.

72. The optical coherence tomography module according to claim 70, wherein the portion of the interferometer and the detector unit are mounted within the optical module casing.

73. An optical coherence tomography module for an optical coherence tomography apparatus, the module comprising:
a light source according to claim 1; and
a sensor arrangement positioned and equipped for sensing properties of light produced by the light source and/or equipped for performing a measurement of an interferometer signal.

74. An optical coherence tomography module for an optical coherence tomography apparatus, the module comprising:
a light source according to claim 5; and
a sensor arrangement positioned and equipped for sensing properties of light produced by the light source and/or equipped for performing a measurement of an interferometer signal.

75. An optical coherence tomography module for an optical coherence tomography apparatus, the module comprising:
a light source according to claim 6; and
a sensor arrangement positioned and equipped for sensing properties of light produced by the light source and/or equipped for performing a measurement of an interferometer signal.

* * * * *